(12) United States Patent
Schwartz et al.

(10) Patent No.: US 6,842,643 B1
(45) Date of Patent: Jan. 11, 2005

(54) METHOD AND APPARATUS FOR RESETTING PROGRAMMING PARAMETERS WITHIN AN IMPLANTABLE MEDICAL DEVICE

(75) Inventors: Allan R. Schwartz, Moorpark, CA (US); David W. Adinolfi, Eden Prairie, MN (US); Hakan Hornell, Lidingoe (SE); Kelly H. McClure, Simi Valley, CA (US); Brian M. Mann, Beverly Hills, CA (US)

(73) Assignee: Pacesetter, Inc., Sylmar, CA (US)

( * ) Notice: Subject to any disclaimer, the term of this patent is extended or adjusted under 35 U.S.C. 154(b) by 150 days.

(21) Appl. No.: 10/051,889

(22) Filed: Jan. 16, 2002

Related U.S. Application Data (63) Continuation of application No. 09/459,258, filed on Dec. 10, 1999, now abandoned.

(51) Int. Cl.[7] .............................................. A61N 1/08
(52) U.S. Cl. ...................................................... 607/30
(58) Field of Search ............................. 607/27, 30, 31, 607/32, 59–61

(56) References Cited

U.S. PATENT DOCUMENTS

| | | | | |
|---|---|---|---|---|
| 5,431,691 A | | 7/1995 | Snell et al. .................... 607/27 |
| 5,456,691 A | * | 10/1995 | Snell ............................ 607/30 |
| 5,836,989 A | * | 11/1998 | Shelton ........................ 607/27 |
| 5,891,178 A | * | 4/1999 | Mann et al. ................... 607/27 |
| 5,893,883 A | * | 4/1999 | Torgerson et al. ............ 607/59 |
| 5,974,341 A | * | 10/1999 | Er et al. ........................ 607/31 |
| 6,073,049 A | * | 6/2000 | Alt et al. ....................... 607/31 |

\* cited by examiner

Primary Examiner—Jeffrey R. Jastrzab
Assistant Examiner—Frances P. Oropeza (57) ABSTRACT

An external programmer is provided with the capability of automatically resetting the programming state of an implantable medical device to a previous programming state. To this end, the pacemaker maintains parameters representative of current and past programming states. In response to a physician-initiated reset function using an external programmer, the pacemaker transfers information pertaining to the programming states to the external programmer along with a pointer identifying the current state. The physician selects one of the previous programming states and the external programmer then updates the pointer to identify the selected state and transmits the pointer back to the pacemaker. The pacemaker accesses the programming parameters stored therein corresponding to the programming state identified by the new pointer and is reprogrammed. Accordingly, the programming state of the pacemaker is reset to the previous programming state without requiring manual reentry of the parameters. The external programmer may also be configured to enable the physician to modify parameters or to display differences between two or more programming states of the medical device. Also, the external programmer may be configured to enable the physician to merge parameters from two or more programming states to create a new programming state.

16 Claims, 10 Drawing Sheets

METHOD AND APPARATUS FOR RESETTING PROGRAMMING PARAMETERS WITHIN AN IMPLANTABLE MEDICAL DEVICE

CROSS-REFERENCE TO RELATED APPLICATIONS

This application is a continuation of U.S. patent application Ser. No. 09/459,258, filed December 10, 1999, and now abandoned.

FIELD OF THE INVENTION

The present invention generally relates to implantable medical devices and to external programmer devices used in connection therewith and in particular to methods and apparatus for programming implantable medical devices using the external programmer device.

BACKGROUND OF THE INVENTION

A wide range of implantable medical devices are provided for surgical implantation into humans or animals. Common examples include the cardiac pacemaker and the implantable cardioverter defibrillator (ICD). Other examples include devices for stimulating or sensing portions of the brain, spinal cord, muscles, bones, nerves, glands or other body organs or tissues.

Implantable medical devices, particularly pacemakers and ICDs, are often configured to be used in conjunction with an external programmer device which allows a physician to program the operation of the device to, for example, control the specific parameters by which the pacemaker detects arrhythmia conditions and responds thereto. For instance, the external programmer may allow the physician to specify the sensitivity with which the pacemaker or ICD senses electrical signals within the heart and to further specify the amount of electrical energy to be employed in administering therapy. Additionally, the external programmer may be configured to receive and display a wide variety of diagnostic information detected by the implantable device, such as electrical heart signals sensed by the device.

Current state of the art implantable medical devices may have dozens or hundreds of parameters that can be individually programmed using the external programmer. The programmable parameters permit the operation of the medical device to be tailored to the needs of the particular patient to provide optimal therapy while minimizing the risk of unnecessary therapy. However, the process of initially programming the many parameters can be a fairly laborious one even when a state of the art external programmer is used. In this regard, to program the many parameters, the physician may need to select numerous individual data entry screens using the external programmer and then manually enter specific parameters using a key pad. To minimize the amount of parameters that need to be manually entered, the external programmer may provide default values for many of the parameters. Nevertheless, for many patients, numerous parameters need to be individually manually entered by the physician. After the parameters have been entered, the external programmer generates programming commands for transmission to the implanted device via a telemetry system. U.S. Pat. No. 5,431,691 to Snell et al. entitled "Method and a System for Recording and Displaying a Sequential Series of Pacing Events" provides a detailed description of the operation of one exemplary pacemaker and external programmer system and is incorporated by reference herein.

Thus, a laborious initial programming procedure often needs to be performed by the physician for each patient receiving an implantable medical device. Unfortunately, in some cases, the parameters need to be subsequently modified. For example, the patient may complain of shortness of breath or other medical problems requiring the physician to repeat some or all of the programming steps to modify the programming parameters. In some cases, the updated programming does not benefit the patient. Accordingly, the physician may need to yet again perform many of the programming procedures to reset the programming to values that had been previously entered. For some patients, over a period of months or years, the programming parameters may need to be frequently modified, then modified again, often returning the programming state of the implantable device to a previous programming state.

Accordingly, it would desirable to provide an external programmer capable of automatically resetting the programming parameters of an implantable medical device to a previously programmed set of parameters such that the device can be easily reset to a previous programming state without re-entry of the programming parameters. Aspects of the present invention are directed to that end.

To facilitate the selection of a previous programming state, it would be desirable to provide the external programmer with the capability to display the differences between two or more programming states or to permit a physician to select a previous programming state and then modify only selected parameters from that state to create a new programming state. It would also be desirable to provide the external programmer device with the capability to merge the parameters from two or more previous programming states to create a new modified programming state. Additionally, some state of the art external programmer devices provide modeling software which models the performance of the implantable medical device based on a particular set of programming parameters and generates graphical displays permitting the physician to easily gauge the expected performance of the device. Thus, it would also be desirable to provide such an external programmer with the capability to display models of the behavior of the implantable medical device based upon two or more selected previous programming states to facilitate selection of the programming state providing the best performance. Other aspects of the invention are directed to these various features.

SUMMARY OF THE INVENTION

The present invention generally relates to implantable medical devices and to external programmer devices used in connection therewith and in particular to methods and apparatus for programming implantable medical devices using the external programmer device.

In accordance with a first aspect of the invention, a device is provided for resetting the programming state of an implantable medical device. The device includes means for maintaining parameters representative of a plurality of programming states including a current programming state and at least one other programming state. Means are also provided for receiving a reset signal for resetting the programming state of the implantable device to a selected one of the other programming states and for resetting the programming of the implantable device to the selected state.

In an exemplary embodiment, the programming parameters for the plurality of programming states are maintained within the implantable medical device. To reset the programming state, the external programmer controls the implanted device to transmit the programming parameters for the plurality of states to the external programmer for storage therein, and then displays information representative of the programming states to a physician operating the external programmer to permit selection of one of the states. After a state has been selected, the external programmer transmits a pointer or other signal identifying the selected state to the implantable device and, in response thereto, the implantable device reprograms its internal functional components in accordance with the selected programming state.

Also in the exemplary embodiment, means are provided to permit the physician to modify any or all of the parameters of the selected state prior to resetting the programming of the implantable medical device. If any of the programming parameters are changed, the external programmer device generates appropriate programming commands for transmission to the implantable device to reflect the updated parameters.

In accordance with a second aspect of the invention, a device is provided for use with an external programmer of an implantable medical device for displaying differences between two or more programming states of the medical device. The device includes means for maintaining parameters representative of a plurality of programming states and means for generating a display indicating the differences, if any, between the selected states. In this manner, a physician operating the external programmer device can easily identify differences between the parameters corresponding to different states to facilitate selection of a particular one of the states.

In accordance with a third aspect of the invention, a device is provided for use with an external programmer of an implantable medical device for merging parameters from two or more programming states to create a new programming state. The device includes means for maintaining parameters representative of a plurality of programming states and means for receiving a merge signal for resetting the programming state to a combination of selected states of the plurality of programming states. Means are also provided for resetting the programming of the implantable device to the combination of the first selected states. In accordance with a fourth aspect of the invention, a device is provided for use with an external programmer of an implantable medical device wherein the external programmer is capable of modeling the behavior of the implantable device based upon sets of programming parameters and is capable of displaying graphs representative of the models.

The device includes means for maintaining parameters representative of a plurality of programming states and means for receiving a compare signal initiating a comparison of device behavior models for selected programming states of the plurality of programming states. The device additionally includes means for generating models for the behavior of the implantable device for the selected programming states based upon the parameters of the selected states and for displaying graphs representative of models generated for the selected states. In this manner, a physician operating the external programmer can easily compare the behavior models for two or more programming states to identify the state which will provide the best performance for the patient. Thereafter, the programming of the implantable medical device can be easily reset to the programming state providing the best expected behavior.

Preferably, the external programmer device is configured to implement all of these aspects of the invention. Method embodiments of the invention are also achieved. Other advantages of the invention are provided as well.

DETAILED DESCRIPTION OF THE INVENTION

The invention relates to improved techniques for programming implantable medical devices. The invention will be described primarily with reference to a pacemaker used in conjunction with an external programmer device, but principles of the invention are applicable to other implantable medical devices such as ICDs and to other external control devices as well.

Figure 1:
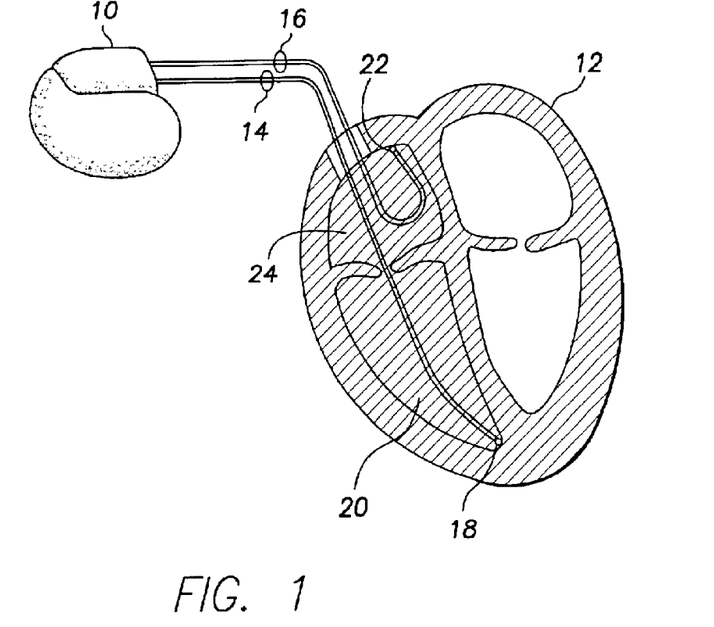
FIG. 1 shows an implantable pacemaker coupled to a heart via a pair of electrical leads.

FIG. 1 illustrates an exemplary implantable pacemaker 10 coupled to a heart 12 by way of a ventricular lead 14 and an atrial lead 16. Ventricular lead 14 includes an electrode 18 positioned in the right ventricle 20 of the heart and atrial lead 16 includes an electrode 22 positioned in the right atrium 24 of the heart. Various internal components of the pacemaker 10 operate to sense the electrical activity of the heart, such as the presence of P-waves and R-waves, using electrodes 18 and 22 and to selectively stimulate the heart in response to events sensed within the heart by conducting electrical stimulation pulses to the heart using the electrodes. The pacemaker 10 may be configured to operate in either a single-chamber mode or a dual-chamber mode.

Figure 2:
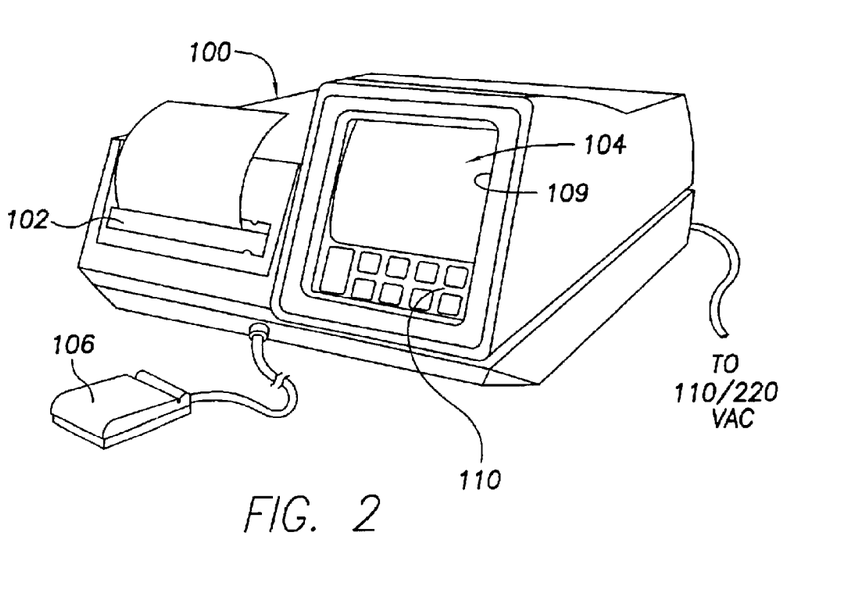
FIG. 2 is a perspective view of an external programmer that may be used for communicating with the implantable pacemaker of FIG. 1.

The operation components of pacemaker 10 of FIG. 1 is programmed by programming signals received from an external programmer (FIG. 2). Table I provides a list of exemplary programming parameters employed by the external programmer to program the operation of the pacemaker 10.

TABLE I

| PROGRAMMING PARAMETER | PROGRAMMED FUNCTION |
| --- | --- |
| Mode | Pacemaker Mode Programmed |
| Base Rate | Heart Base Rate Programmed |
| Rest Rate | Heart Rest Rate Programmed |
| Maximum Tracking Rate | Maximum Pacemaker Tracking Rate Programmed |
| Maximum Sensor Rate | Maximum Pacemaker Sensor Rate Programmed |
| Rate Responsive AV/PV Delay | Rate Responsive AV/PV Delay Programmed |

Programming parameters received from the external programmer 100 are stored within the pacemaker 10. More specifically, parameters corresponding to a particular programming session are stored together, along with any default parameters, within the pacemaker 10 as a unique programming state. Whenever a new programming session is initiated to modify or otherwise update the programming parameters, the modified parameters, along with previously programmed or default parameters, are stored within the pacemaker 10 as a new programming state. Accordingly, after a number of programming sessions, the pacemaker 10 stores a number of programming states corresponding to the number of programming sessions. The pacemaker 10 also stores a pointer identifying which of the programming states is the current programming state. Typically, the pointer indicates that the most recent programming state is the current state. As will be described in greater detail below, the external programmer 100 is configured to cause the pacemaker 10 to reset the current programming state to one of the previous programming states, i.e., the external programmer 100 can transmit signals causing the pointer identifying the current state to be reset, i.e., altered, to one of the other states. In response thereto, pacemaker 10 reprograms the operation of its internal components in accordance with the parameters of the programming state identified by the new pointer.

FIG. 2 illustrates an exemplary external programmer 100 configured for programming pacemaker 10 (FIG. 1) and for displaying information received from the pacemaker 10 such as diagnostic information. External programmer 100 includes a printer 102 for printing out a graphical representation of the information received from the pacemaker 10 and a display screen 104 for providing a graphical representation of the information such as, for example, an intracardiac electrogram (IEGM). The programming of the pacemaker 10 and the generation of graphic displays of information received from the pacemaker 10 is subject to the control of a physician or other user operating the external programmer 100. To this end, external programmer 100 presents various menus on display screen 104 for use in controlling operation of the external programmer 100 to program pacemaker 10 (FIG. 1) using any of the parameters listed above in TABLE I. Various menus are also presented on display screen 104 for use in controlling operation of the external programmer 100 to generate displays on display screen 104 of parameters used to the pacemaker 10. External programmer 100 preferably receives menu selections from the physician through a touch screen 109 which overlays display screen 104. The actual programming of the pacemaker 10 is achieved using telemetry head 106 which includes telemetry circuitry 107 coupled to a telemetry wand 108 (see FIG. 10) which, in use, is placed in proximity to the pacemaker 10. While it is presently preferred that the telemetry circuitry 107 be remotely coupled, e.g., via a cable, to the telemetry wand 108, the distribution of the associated circuitry of the telemetry head 106 between the telemetry circuitry 107 and the telemetry wand 108 is not significant to the application of the present invention.

As noted, the external programmer 100 is also configured to permit a physician operating the external programmer 100 to reset a current programming state of the pacemaker 10 to a previous programming state. The external programmer 100 also provides a set of related functions applicable to the various programming states. More specifically, the external programmer 100 may provide one or more of the following additional functions: (1) after the pacemaker 10 has been reset to a previous programming state, the external programmer 100 can reset the ill pacemaker 10 to one of the programming states originally programmed subsequent to the newly reset state; (2) the external programmer 100 permits the pacemaker 10 to be set to a new programming state based upon a previous programming state wherein one or more programming parameters are modified; (3) the external programmer 100 permits the pacemaker 10 to be set to a new programming state based upon a combination of two other programming states; (4) the external programmer 100 permits a physician using the external programmer 100 to display differences between selected programming states; and (5) the external programmer 100 permits the physician operating the external programmer 100 to display graphical models of the expected behavior of two or more programming states.

Figure 3:
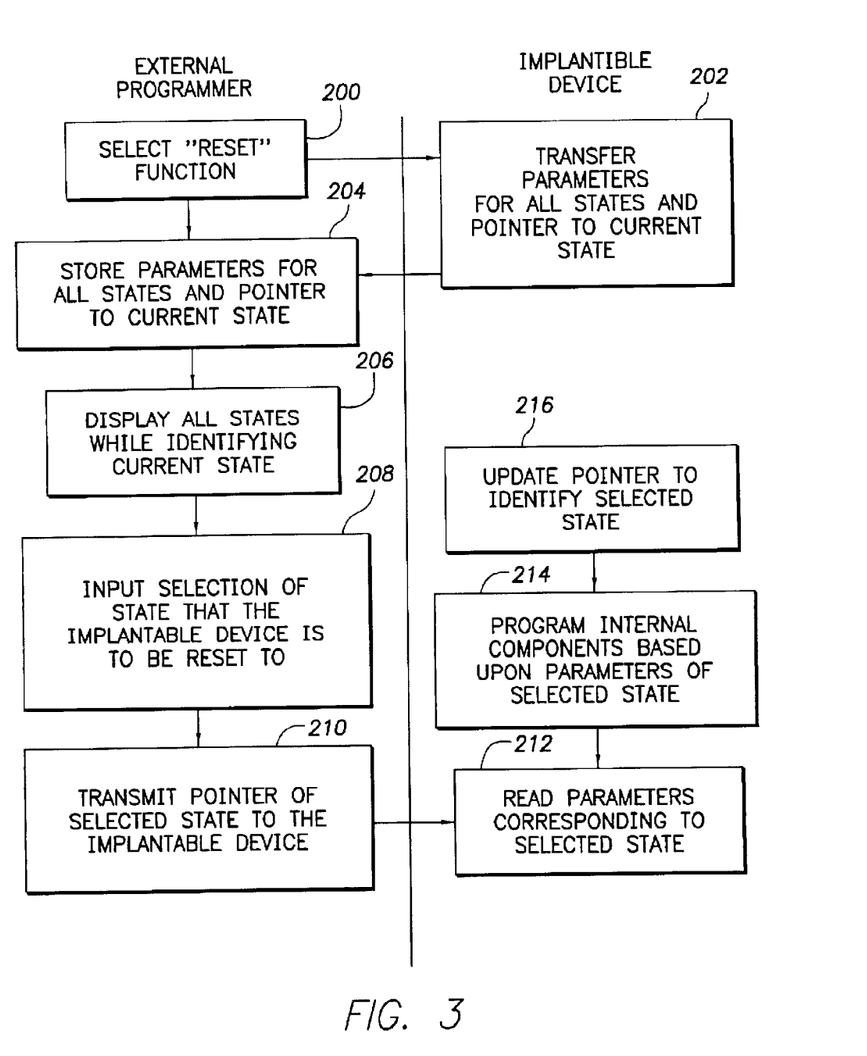
FIG. 3 is a flow chart illustrating steps performed by both the external programmer and implantable device of FIGS. 1 and 2 for use in resetting a programming state of the implantable device to a previously programmed state.

With reference to FIGS. 3 and 6–9, the methods employed by the external programmer 100 and pacemaker 10 to provide the aforementioned functionality will now be described. FIG. 3 illustrates exemplary steps performed by the external programmer 100 and pacemaker 10 of FIGS. 1 and 2 for use in resetting the programming state of the pacemaker 10 to a previous state or, if the external programmer state has already been reset to a previous state, to reset the pacemaker 10 to one of the subsequently programmed states. Initially, at step 200, the physician operating the external programmer 100 selects a reset command from a menu presented by the external programmer 100. In response to the reset command, the external programmer 100 sends a command to the pacemaker 10 through the telemetry head 106 for controlling the pacemaker 10 to transmit the parameters for all of the programming states stored within the pacemaker 10 to the external programmer 100. In response thereto, the pacemaker 10 transfers the parameters for all states at step 202 and the parameters are stored within the external programmer 100 at step 204. In the alternative, parameters can be automatically transferred whenever a communication session between the external programmer 100 and the pacemaker 10 is initiated, for example, to transfer the programming parameters along with other operational parameters such as the model and serial number of the implanted device and any historical information pertaining to the patient stored within the device.

In any case, the pacemaker 10, at step 202, also transfers a pointer identifying the current programming state of the pacemaker 10 for storage along with the programming states in step 204. In many cases, the pointer will merely identify the most recent programming state of the pacemaker 10. However, if the programming state has previously been reset by the external programmer 100, then the pointer will identify one of the earlier programming states as the most current state.

Figure 4:
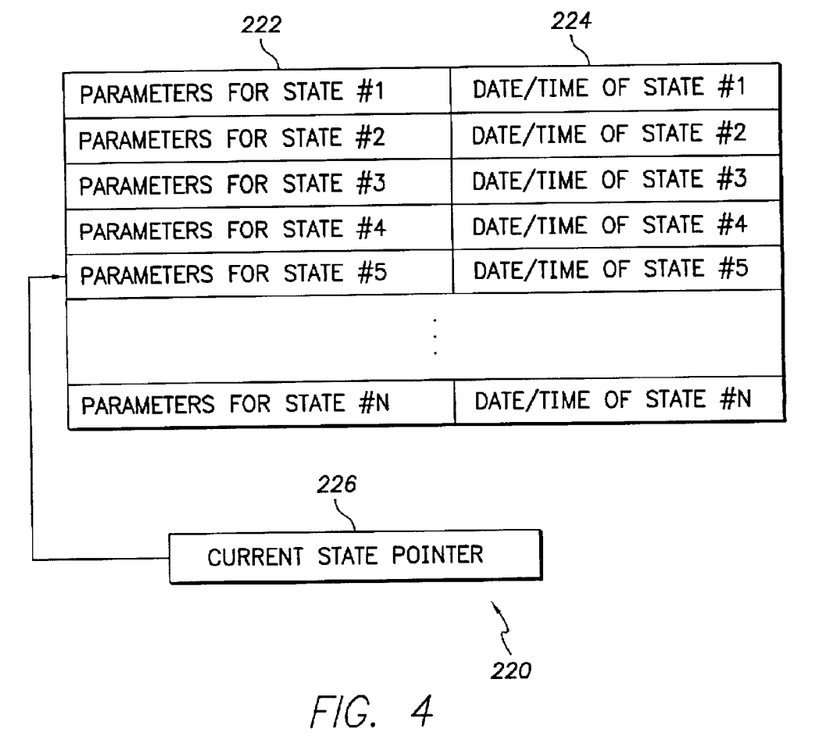
FIG. 4 is a block diagram illustrating a memory unit used in coordination with the implantable medical device for use in storing a set of programming states to permit a current programming state of the device to be reset to another state using the method of FIG. 3.

FIG. 4 illustrates an exemplary memory unit 220 of the pacemaker 10 employed to store the various programming states. Preferably, the memory unit 220 is contained within a parameter storage unit 120 within the pacemaker 10. Alternatively, the memory storage unit 220 can be contained within a portion of a parameter storage unit 133 within the external programmer 100 (see FIG. 10). For each programming state, the memory unit stores all of the parameters 222 for that state including parameters that were specifically entered as well as any default parameters. Additionally, the memory unit 220 stores the date and time 224 that the pacemaker 10 was programmed to the corresponding state. The memory unit 220 also stores a pointer 226 identifying the current programming state of the pacemaker 10. Note that any two programming states may differ from one another by only a single parameter or by many parameters. In some cases, every parameter of a particular state will differ from all of the parameters of the other programming states.

Figure 5:
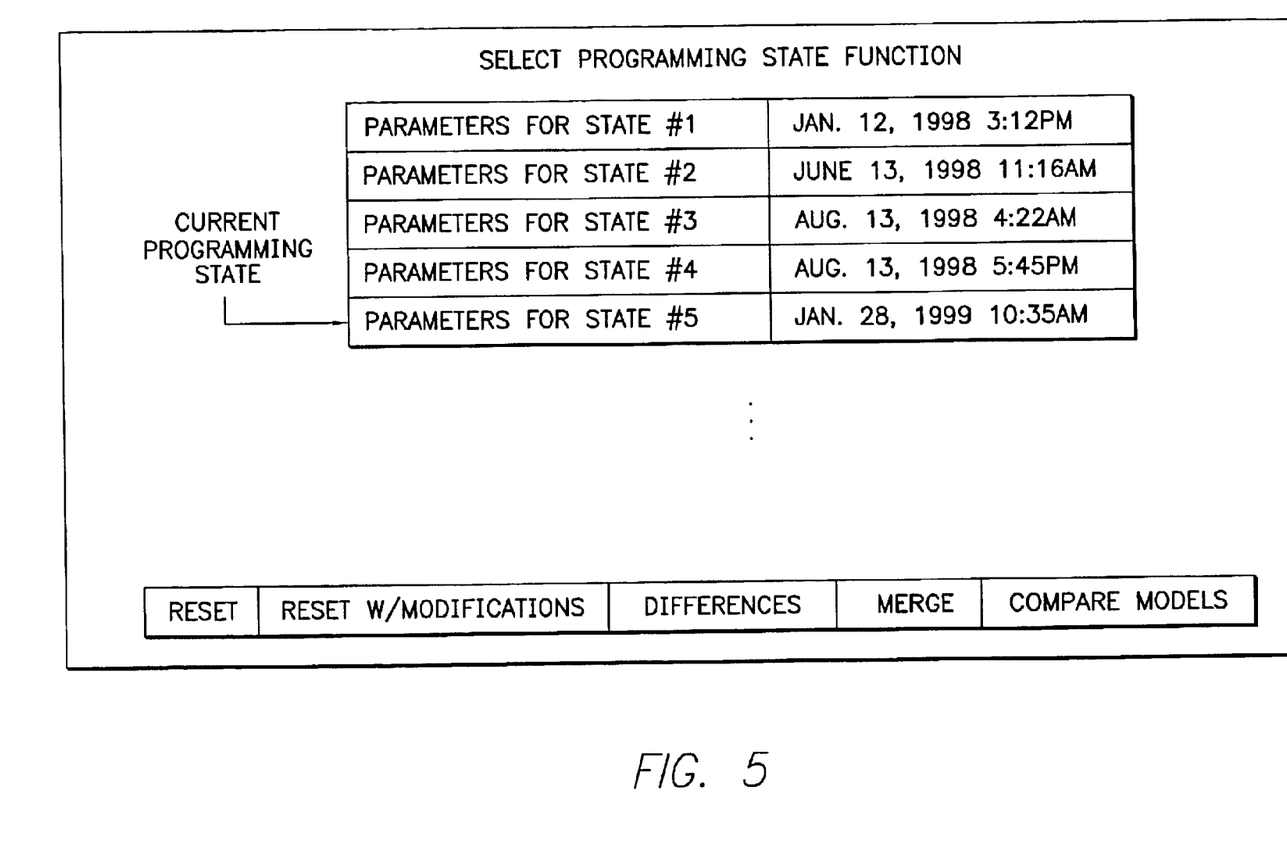
FIG. 5 is a exemplary display screen presented by the external programmer of FIG. 2 displaying a set of previous programming states and sets of functions to be performed using the previous programming states in accordance with the method of FIG. 3.

Referring again to FIG. 3, at step 206, the external programmer 100 displays the programming parameters of all of the programming states 222 transmitted from the pacemaker 10 along within the identification of the current state. FIG. 5 illustrates an exemplary display screen presented by the external programmer 100 listing the various programming states. As can be seen, an arrow identifies the current programming state. In the example of FIG. 5, all of the parameters corresponding to each state are not concurrently displayed. However, if desired, a physician operating the external programmer 100 may select a function entitled "DISPLAY DETAILS" (not shown) to cause the external programmer 100 to display all of the parameters corresponding to the selected state.

Continuing with FIG. 3, at step 208, the external programmer 100 receives a pacemaker 10 state selection from the physician. In the example of FIG. 5, the physician may select, for example, the state identified as state "#5". Depending upon the particular programming of the external programmer 100, this may be accomplished by using arrow keys on the keyboard 110 of the external programmer 100 to scroll through the list of states until a desired state is highlighted, and then pressing "enter". Once the state has been selected by the physician, the external programmer 100, at step 210, generates and transmits a command to the pacemaker 10 to reset the programming state to the selected state. The command includes a pointer identifying the selected state. In response thereto, the pacemaker 10, at step 212, reads the parameters corresponding to the selected state from its memory unit. Then, at step 214, the pacemaker 10 reprograms its internal components based upon those parameters. Finally, at step 216, the pacemaker 10 updates the pointer 226 stored in the memory unit 220 to identify the selected state.

Thus, the physician operating the external programmer 100 easily and conveniently resets the programming of the pacemaker 10 to a different programming state by merely selecting the state and entering the appropriate reset commands. Hence, with only a few keystrokes, the physician may reset dozens of parameters of the pacemaker without the need to individually enter any of the parameters and without risk of inadvertent programming errors that could otherwise occur if the physician were required to enter all programming parameters.

Finally, at step 218, the pacemaker 10 sends an acknowledgment signal back to the external programming acknowledging that the programming state of the pacemaker 10 had been reset to the selected state and, in response thereto, the external programmer 100 displays the acknowledgment on the display screen 104 for viewing by the physician.

Figure 6:
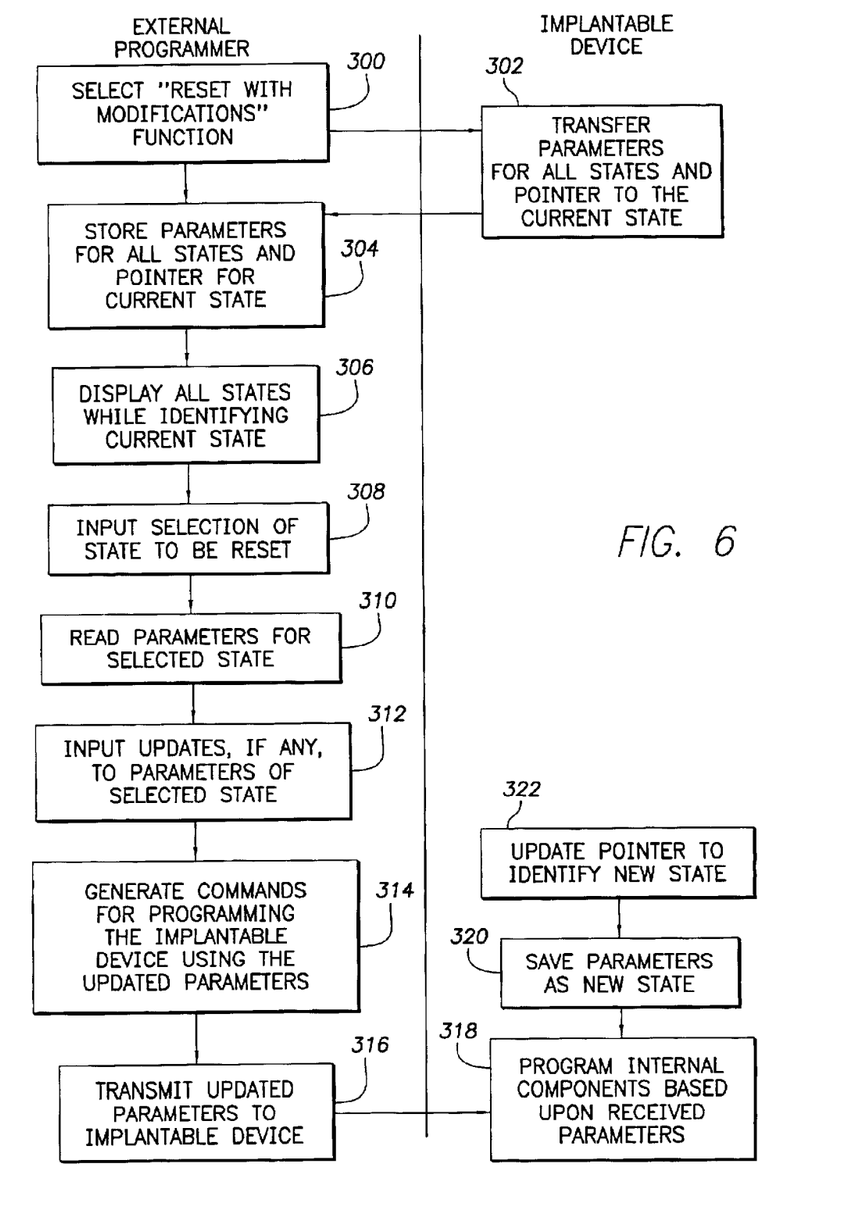
FIG. 6 is a flow chart illustrating steps performed by the external programmer and implantable device of FIGS. 1 and 2 for use in resetting the programming state of the implantable device to another programming state while also permitting selected parameters to be updated prior to reprogramming.

In some circumstances, the physician may wish to reset the programming state of the pacemaker 10 to a previous state while changing some or all of the programming parameters. FIG. 6 illustrates steps performed by the external programmer 100 and pacemaker 10 for implementing this function. Many of the steps of FIG. 6 are similar to those of FIG. 3. Accordingly, only pertinent differences will be described in detail.

After the reset function is selected in step 300, the parameters for all of the states and the pointer 226 identifying the current state are transferred from the pacemaker 10 to the external programmers 100 using steps 302 and 304. The external programmer 100 then displays all states along with an identification of the current state (e.g., as seen in FIG. 5). If the states have already been transferred to the external programmer 100, perhaps during the processing of a previous reset command, then it is not necessary to repeat the transfer. The physician then selects a "RESET WITH MODIFICATIONS" function at step 308 and selects a state. At step 310, the external programmer 100 reads all parameters for the selected state and presents a list of the parameters on the display screen (not separately shown). At step 312, the physician enters updates to any of the parameters. Depending upon the programming of the external programmer 100, this may be achieved by scrolling through the parameters using the arrow button of the keyboard 110 until a selected parameter is highlighted, then manually typing in new numerical values for the selected parameter. In other implementations, the physician may select from a list of preprogrammed acceptable values for each programming parameter.

Once any or all of the parameters of the selected state have been updated, the external programmer 100 generates, at step 314, commands for reprogramming the modified parameters within the pacemaker 10. These commands may be the same type of commands used to initially program the pacemaker 10. At step 316, the commands are transmitted to the pacemaker 10 which, at step 318, responds by programming its internal components based upon the commands. At step 320, the pacemaker 10 stores all of the parameters corresponding to the selected state, as modified, as a new state. At step 322, the pointer identifying the current state is updated to identify the new state.

Thus, unlike the embodiment of FIG. 3 wherein the pacemaker 10 merely updates its internal pointer 226 to identify the selected state, in the embodiment of FIG. 6, a new state is stored and the pointer is set to identify the new state. Depending upon the particular implementation, when transmitting parameters to the pacemaker 10 at step 316, the external programmer 100 may either selectively transmit programming commands corresponding to only those parameters that were modified or may transmit programming commands corresponding to all programmable parameters associated with the selected state. If all parameters are not transmitted, then the pacemaker 10, when creating the new programming state, reads all unmodified parameters corresponding to the selected state from the memory unit and copies those parameters into the new state. As can be appreciated, a wide variety of particular implementations may be provided consistent with the general principles of the invention.

Thus, FIG. 6 provides a method for creating a new state based upon a previous state while updating some or all of the programming parameters. The method of FIG. 6 is particularly helpful whenever the physician wishes to set the pacemaker 10 to a new state which is very similar to a previous state but differs only with respect to a few parameters.

Figure 7:
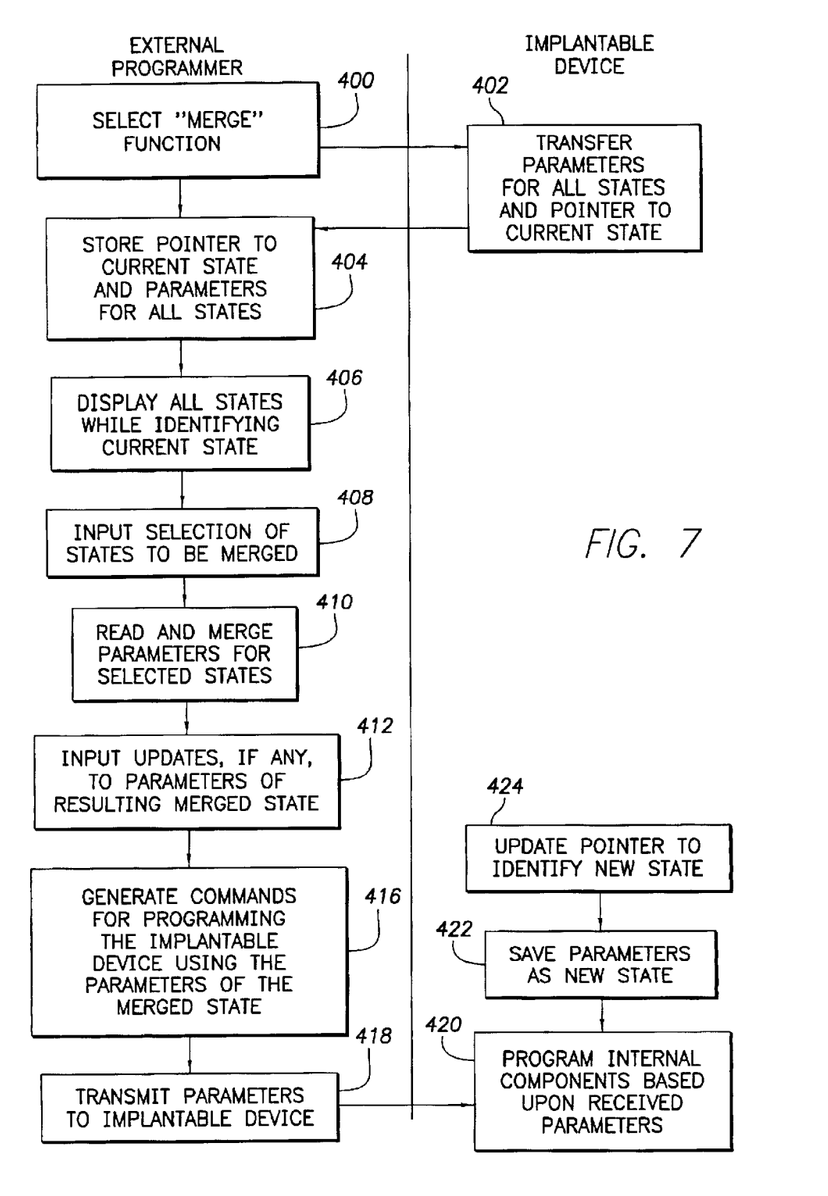
FIG. 7 is a flow chart of steps performed by the external programmer and implantable device of FIGS. 1 and 2 for use in permitting the programming parameters of two or more states to be merged together to create a new programming state.

In other circumstances, the physician may wish to set the pacemaker 10 to a new programming state which is a combination of two previous programming states. For example, the physician may wish to set the pacemaker 10 to a state which combines all of the non-default parameters of one state and all of the non-default parameters of another state. To this end, the physician selects the "MERGE" function from the display screen of FIG. 5 in step 400 and, in response thereto, the pacemaker 10 and external programmer 100 perform steps 402 through 406 to transfer parameters corresponding to all states from the pacemaker 10 to the external programmer 100 and to display the states using the external programmer 100. As before, if the states have already been transferred to the external programmer 100, it may not be necessary to repeat the transfer. At step 408, the physician selects two or more states to be merged together to create a new state. At step 410, the external programmer 100 reads the parameters corresponding to all of the selected states and merges the parameters together.

In the preferred implementation, merging is performed as follows. The external programmer 100 first identifies all parameters which are exactly the same in both programming states and copies those parameters into the new state. Then, the external programmer 100 identifies any parameters which differ from the corresponding parameter of the other state to determine whether the parameter in one of the two states is a default parameter and, if so, the external programmer 100 uses the non-default parameter as the new parameter for the new state. Thus, non-default parameters take precedence over default parameters. In the event the parameters for the two states are both non-default parameters, then the external programmer 100 selects the parameter having the more recent update time. Thus, more recently programmed parameters take precedence over earlier programmed parameters. In other implementations, different priority rules may be employed.

At step 412, the external programmer 100 accepts updates, if any, from the physician to the parameters of the merged state. Once updates have been entered, the external programmer 100 then generates programming commands for programming the pacemaker 10 to the new merged state at step 416 and transmits the commands to the pacemaker 10 at step 418. The pacemaker 10 receives the commands, reprograms its internal components based upon the parameters provided therein, saves the parameters as a new state, and updates the pointer 226 to identify the new state using steps 420 through 424.

Thus, FIG. 7 illustrates a method for creating a new state by merging two previous states. Merging is particularly useful when the physician wishes to reprogram the pacemaker 10 to a combination of previous states without needing to re-enter a potentially large number of parameters.

Figure 8:
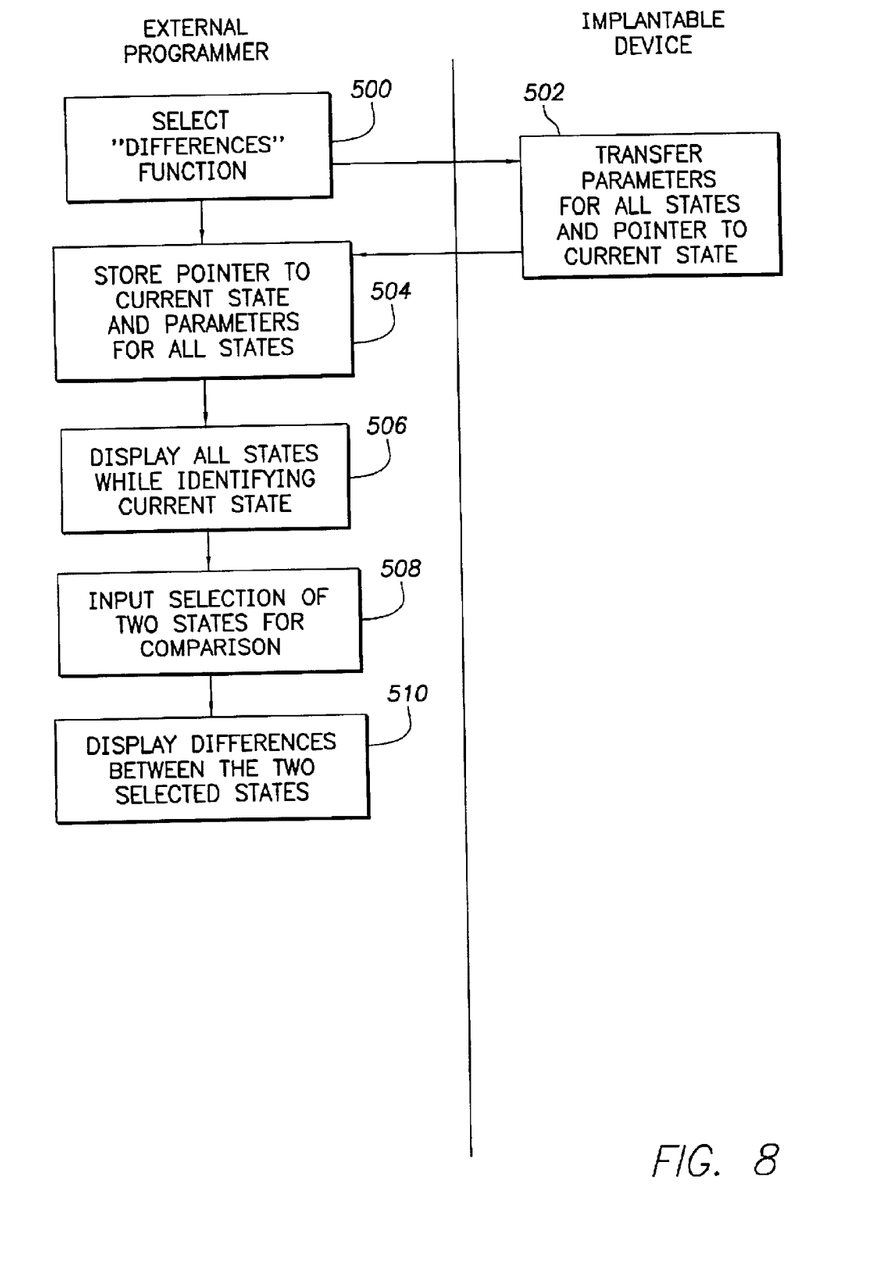
FIG. 8 is a flow chart illustrating method steps performed by the external programmer and implantable device of FIGS. 1 and 2 for use in permitting a comparison of the differences between two or more selected programming states to be displayed on the external programmer.

In some circumstances, the physician may merely wish to view the differences between two states and, if so, the physician selects, at step 500, the "DIFFERENCES" function from the display of FIG. 5. In response thereto, the external programmer 100 and pacemaker 10 perform the steps of FIG. 8. As before, parameters corresponding to all states and a pointer identifying the current state are transmitted (if not already stored in the external programmer 100) from the pacemaker 10 to the external programmer 100 and displayed thereon using steps 502 through 506. At step 508, the external programmer 100 receives a selection of two or more states for comparison and reads the parameters corresponding to the two selected states. At step 510, the external programmer 100 examines the parameters to identify any differences and displays an indication of those differences on a display screen (not shown). Depending upon the particular programming of the external programmer 100, the external programmer 100 may display only those parameters which differ or may display all parameters while highlighting those which differ. The method of FIG. 8 is particularly useful to display differences between two states prior to selecting which states are to be merged together.

Figure 9:
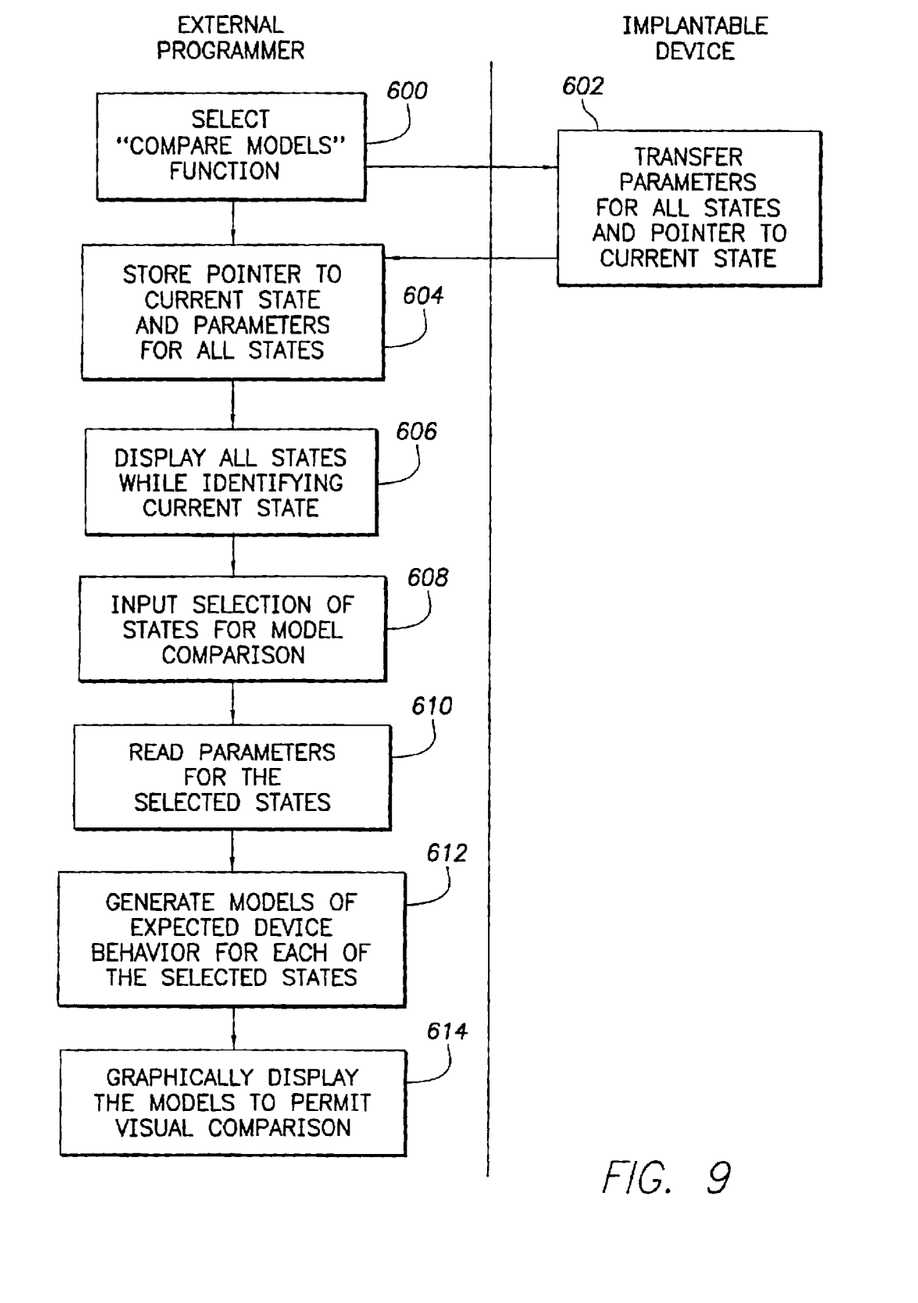
FIG. 9 is a flow chart illustrating steps performed by the external programmer and implantable device of FIGS. 1 and 2 for use in displaying a comparison of models of the behavior of two or more selected programming states using the external programmer.

If the external programmer 100 is provided with software for modeling the behavior of the pacemaker 10 based upon a set of programming parameters, then it may be desirable for the physician to display a comparison of the behavior models for two different programming states using the external programmer 100. If so, the to physician selects, at step 600, the "COMPARE MODELS" function from the display screen of FIG. 5 and, in response thereto, the steps illustrated in FIG. 9 are performed by the pacemaker 10 and the external programmer 100. As before, the pacemaker 10 transfers parameters corresponding to all programming states to the external programmer 100 for storage and display thereon using steps 602–606. At step 608, the physician selects two or more states for model behavior comparison. At step 610, the external programmer 100 reads the parameters corresponding to the selected states and, at step 612, generates models of the expected behavior of the pacemaker 10 for each of the selected states.

At step 614, the external programmer 100 graphically displays the behavior models for the selected states to permit the physician to quickly and easily evaluate differences in the expected behavior. The compare models function thus enables a physician to quickly compare the expected behavior for two or more programming states and can be used, for example, to help the physician identify one particular state for use in resetting the pacemaker 10 or for identifying two or more states for merging.

Figure 10:
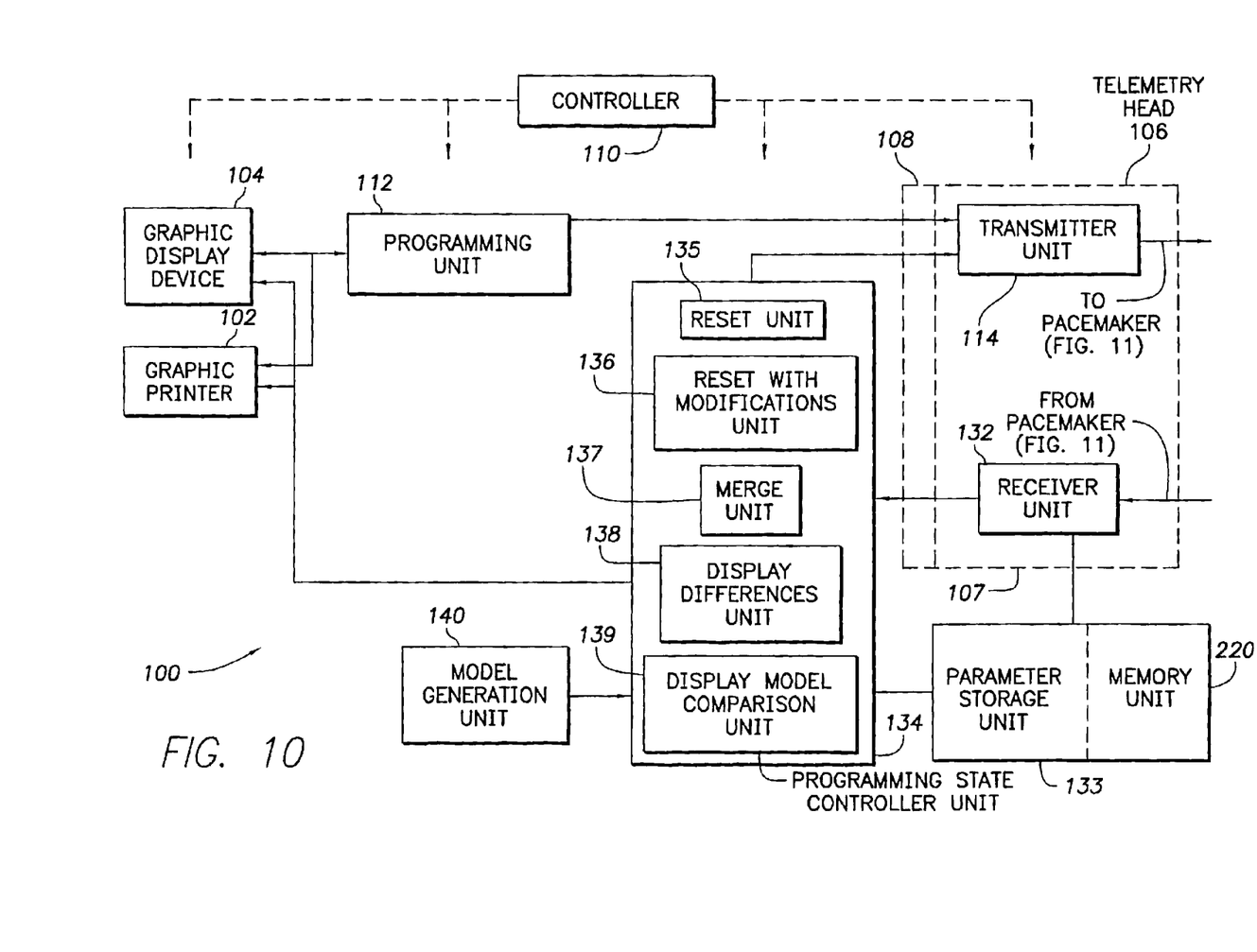
FIG. 10 is block diagram of the primary components of the external programmer of FIG. 2.
Figure 11:
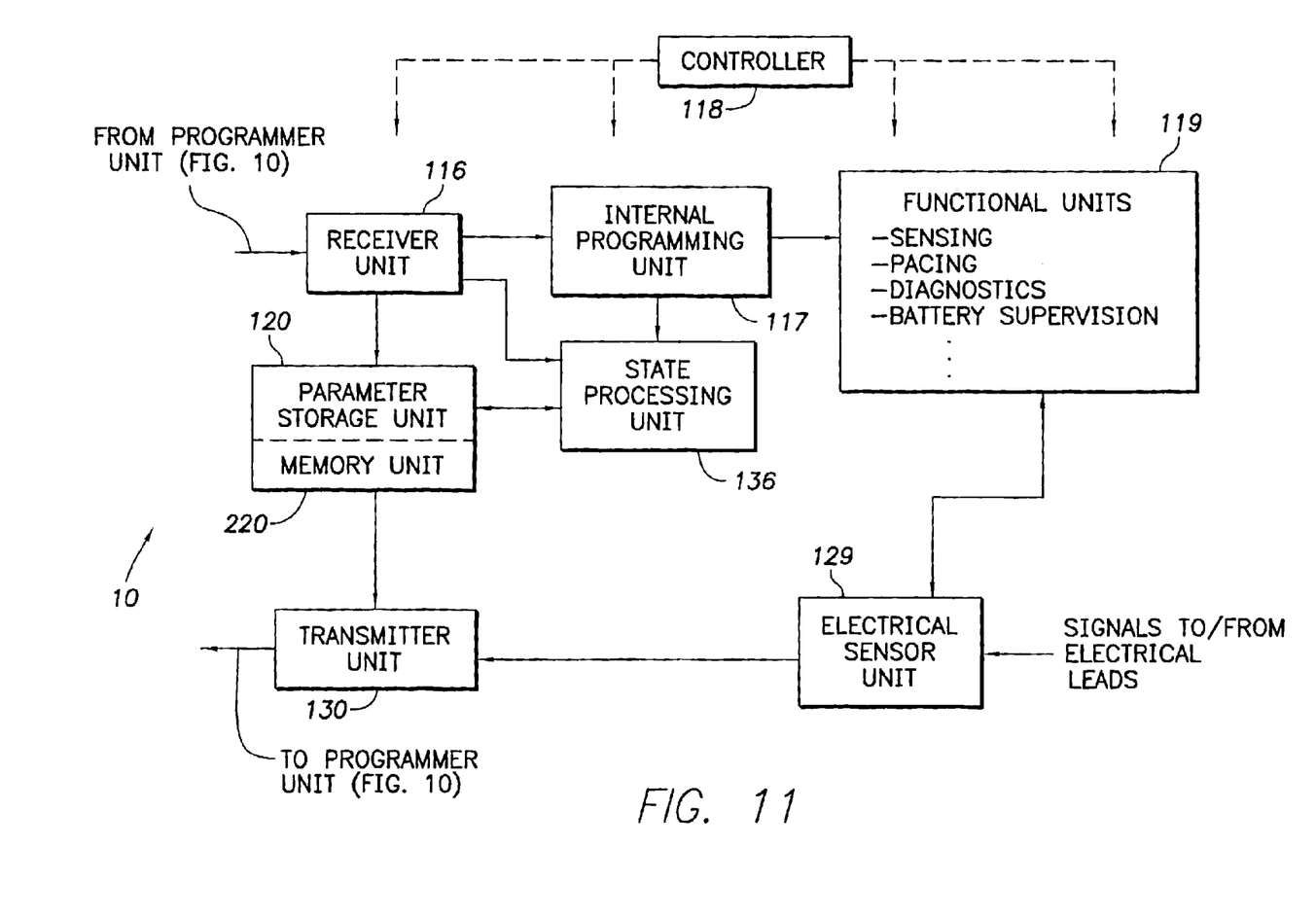
FIG. 11 is block diagram of the primary components of the implantable pacemaker of FIG. 1.

FIGS. 10 and 11 are block diagrams illustrating the primary components of the pacemaker 10 and external programmer 100 of FIGS. 1 and 2 for use in performing the various methods described above in FIGS. 3 and 6–9. More specifically, FIG. 10 illustrates pertinent components of the external programmer 100 and FIG. 11 illustrates pertinent components of the pacemaker 10. The components shown in FIGS. 10 and 11 will be briefly described.

Referring first to FIG. 10, a controller 110 of external programmer 100 controls the graphic display device 104 to display the aforementioned menus from which the physician may select, among other options, to initially program the pacemaker 10, to reset programming parameters to an earlier programming state or to perform any of the other programming state functions described above.

The physician initially programs the pacemaker 10 following its implantation by using a programming unit 112 which controls the graphic display device 104 to display a list of the programming options corresponding to, for example, the programming options listed in TABLE I. The physician selects one or more of the programming options from the list then enters any pertinent parameters such as the applicable pacing mode, rate values or delay values from one or more display screens (not separately shown) presented by the programming unit 112 using the graphic device 104. A transmitter unit 114 of telemetry head 106 transmits appropriate command signals to the pacemaker 10 to program the pacemaker 10 in accordance with the selected options. The physician may also enter patient data such as the name of the patient, any medications prescribed to the patient, any diagnoses of conditions of the patient, and the identification of any electrical leads or other accessory devices used in connection with the pacemaker 10. This information is entered via the display screens of the external programmer 100 and then transferred to the pacemaker 10 along with the programming commands.

Referring to FIG. 11, the programming commands transmitted by the external programmer 100 are received by a receiver unit 116. A controller 118 operates in response to the received commands to program appropriate pacemaker functional units 119 to operate in accordance with the programming parameters using an internal programming unit 117. Additionally, the programming parameters are forwarded by the receiver unit 116 to a parameter storage unit 120 which stores information pertaining to the received programming parameters as an initial programming state. The parameter storage unit 120 may be configured in part as the memory storage unit 220 as shown in FIG. 4. The pacemaker 10 may be configured to employ default parameters in case any specific parameters are not transmitted to the pacemaker 10. In such a case, the default parameters are also stored as part of the programming state in the storage unit 120 under the control of the controller 118.

If one or more programming parameters are subsequently to: reprogrammed, then the parameters corresponding to the modified programming state are also stored within the parameter storage unit 120 as a new state. The programming parameters for the previous state are retained as well. Pointer 226, as shown in FIG. 4, is set to identify the new state as the current state. After several reprogramming sessions, several programming states are stored in storage unit 120. A circular buffer may be employed for the parameter storage unit 120 for storing programming states such that the earliest states may be ultimately overwritten.

Eventually, the physician may need to reset the programming state to a previous programming state or to perform one of the other aforementioned programming state functions. To reset the programming parameters, the physician selects RESET using a menu, such as that shown in FIG. 5. Controller 110 of the external programmer 100 of FIG. 10 forwards appropriate retrieval commands to the pacemaker 10 (FIG. 4) via the transmitter unit 114 of the telemetry head 106. The retrieval commands are received by the receiver unit 116 of the pacemaker 10 of FIG. 11 and forwarded to the parameter storage unit 120 which, in turn, retrieves all stored programming parameters for all states along with the pointer to the current state for transmission to the external programmer 100 via a transmitter unit 130. The various programming state parameters and the pointer are received by a receiver unit 132 of the telemetry head 106 of the external programmer 100 of FIG. 10, stored in a parameter storage unit 133 and also forwarded to a programming state controller unit 134.

Programming state controller unit 134 operates to perform the reset function, as described in detail above, using a reset unit 135. To this end, the reset unit 135 generates a display such as the one shown in FIG. 5 listing all of the programming states along with the pointer identifying the current state and accepts user input identifying the state to which the pacemaker 10 is to be reset. In response thereto, the reset unit 135 sets the pointer to the selected state and forwards the pointer to transmitter unit 114 for transmission to the pacemaker 10. Receiver unit 116 of the pacemaker 10 (FIG. 11) receives the pointer and forwards the pointer to a state processing unit 136 which accesses parameter storage unit 120 to read out the parameters corresponding to the state identified by the transmitted pointer. The state processing unit then forwards the parameters to internal programming unit 117 for reprogramming functional units 119 of the pacemaker 10. Once the functional units 119 have been reprogrammed, a confirmation signal is sent under the control of the state processing unit 136 to the external programmer 100 for display thereon. Referring again to FIG. 10, programming state controller unit 134 additionally includes a reset with modifications unit 136, a merge unit 137, a display differences unit 138 and a display model comparison unit 139 which operate to perform the functions described above in FIGS. 6–9, respectively. As these functions have already been described in detail, they will not be further described herein, other than to note that the display model comparison module employs a model generation unit 140 to generate models of the behavior of the pacemaker 10 based upon the parameters of selected programming states.

Alternative configurations of the present invention should be apparent to one of ordinary skill in the art. For example, in a preferred embodiment, the current state pointer is modified to select the current operating configuration. In an alternative configuration, the order of the operating configurations in the parameter storage unit 120 could be used to define the current operating configuration. For example, the first location (or other predefined location) could be the current operating configuration. Accordingly, the current operating configuration could be reset, i.e., modified, by changing the order of the operating configurations in the parameter storage unit 120. This function could be accomplished by the external programmer 100 reordering (according to the selected operating configuration) the data received from the parameter storage unit 120 and then generating a reset signal that transferred the newly ordered parameter data back to the parameter storage unit 120 in the implantable medical device 10. Accordingly, the current operating configuration of the implantable medical device 10 would be reset.

In the presently preferred embodiment, a plurality of operating configurations are stored within the memory storage unit portion 220 of the parameter storage unit 120 of the pacemaker 10. This enables the use of a different external programmers since the previously used operating configurations would be stored in the implantable medical device 10. In an alternative embodiment, the operating configurations could instead be stored within the memory storage unit portion 220 of the parameter storage unit 133 of the external programmer, e.g., in a semiconductor memory device or on a hard disk.

What has been described are systems for resetting the programming of a pacemaker. The various functional components of the exemplary system may be implemented using any appropriate technology including, for example, microprocessors running software programs or application specific integrated circuits (ASICs) executing hard-wired logic operations. Although described with respect to pacemakers and ICDs used in conjunction with an external programmer, aspects of the invention are applicable to other systems, such as systems employing other implantable medical devices or systems employing other types of external interfaces for use with the implantable device. The exemplary embodiments of the invention described herein are merely illustrative of the invention and should not be construed as limiting the scope of the invention. For example, while an exemplary use with a two-lead implantable pacemaker has been shown, one of ordinary skill in the art would readily appreciate the applicability of the present invention to an implantable cardiac stimulation device that used more than two leads, e.g., an implantable cardioverter defibrillator (ICD) or a pacemaker that stimulated/monitored more than two chambers (for example all four chambers) of the heart individually. Consequently, the present invention is defined by the appended claims.

What is claimed is:

1. An implantable medical device comprising:

a parameter storage unit that is operative to store parameter data corresponding to at least two programming states;

a receiver that is operative to receive communication signals from an external device; and a controller that is connected to the parameter storage unit and to the receiver and that controls the operation of the implantable medical device according to a selected one of the programming states, wherein the controller is responsive to receipt of a reset signal by the receiver to retrieve parameter data from the parameter storage unit corresponding to another of the programming states and to implement the parameter data to change the programming state;

wherein the programming states in the parameter storage unit are ordered such that one of the stored programming states is selected according to its order in the parameter storage unit as a current programming state.

2. The device of claim 1, wherein the parameter storage unit comprises a current state pointer for identifying a current programming state.

3. The device of claim 1, wherein the receiver is configured to communicate with an external programmer.

4. The device of claim 1, wherein the at least two programming states comprise at least three programming states.

5. The device of claim 4, wherein the at least three programming states comprises a current programming state and at least two other programming states.

6. The device of claim 1, further comprising a transmitter to transmit data from the parameter storage unit to the external device, the external device displaying the differences between the selected programming states received from the parameter storage unit.

7. The device of claim 1, wherein the parameter storage unit stores all the parameter data for the implantable medical devise for each of the programming states.

8. The device of claim 7, wherein the parameter data comprises mode, base rate, rest rate, maximum tracking rate, maximum sensor rate, and rate responsive AV/PV delay.

9. An implantable medical device comprising:

a parameter storage unit that is operative to store parameter data corresponding to at least two programming states:

a receiver that is operative to receive communication signals from an external device:

a controller that is connected to the parameter storage unit and to the receiver and that controls the operation of the implantable medical device according to a selected one of the programming states, wherein the controller is responsive to receipt of a reset signal by the receiver to retrieve parameter data from the parameter storage unit corresponding to another of the programming states and to implement the parameter data to change the programming state; and a transmitter to transmit data from the parameter storage unit to the external device, the external device to select at least two of the programming states received from the parameter storage unit to form a new programming state, the new programming state to become the current programming state.

10. A method for controlling operation of an implantable medical device, the method comprising:

maintaining at least three sets of parameters representative of at least three programming states comprising a current programming state and at least two other programming state;

receiving a reset signal for resetting the programming state of the implantable device:

retrieving a corresponding set of parameters based on the received reset signal:

implementing the retrieved set of parameters to alter the operation of the implantable device; and transmitting the at least three sets of parameters to an external device to form a new programming state, the new programming state to become the current programming state.

11. The method of claim 10, wherein receiving a reset signal comprises receiving a reset signal from an external programmer.

12. The method of claim 10, wherein receiving a reset signal comprises receiving a reset signal corresponding to one of the programming states.

13. The method of claim 10, wherein implementing the retrieved set of parameters comprises programming functional components of the implantable device in accordance with the parameters of the selected programming state.

14. The method of claim 10, further comprising transmitting the at least three sets of parameters to the external device to display the differences between at least two sets of parameters.

15. The method of claim 10, wherein the at least three sets of parameters comprise all the parameter data for the at least three programming states of the implantable medical device.

16. The method of claim 15, wherein the parameter data comprises mode, base rate, rest rate, maximum tracking rate, maximum sensor rate, and rate responsive AV/PV delay.

* * * * *